Figure 1:
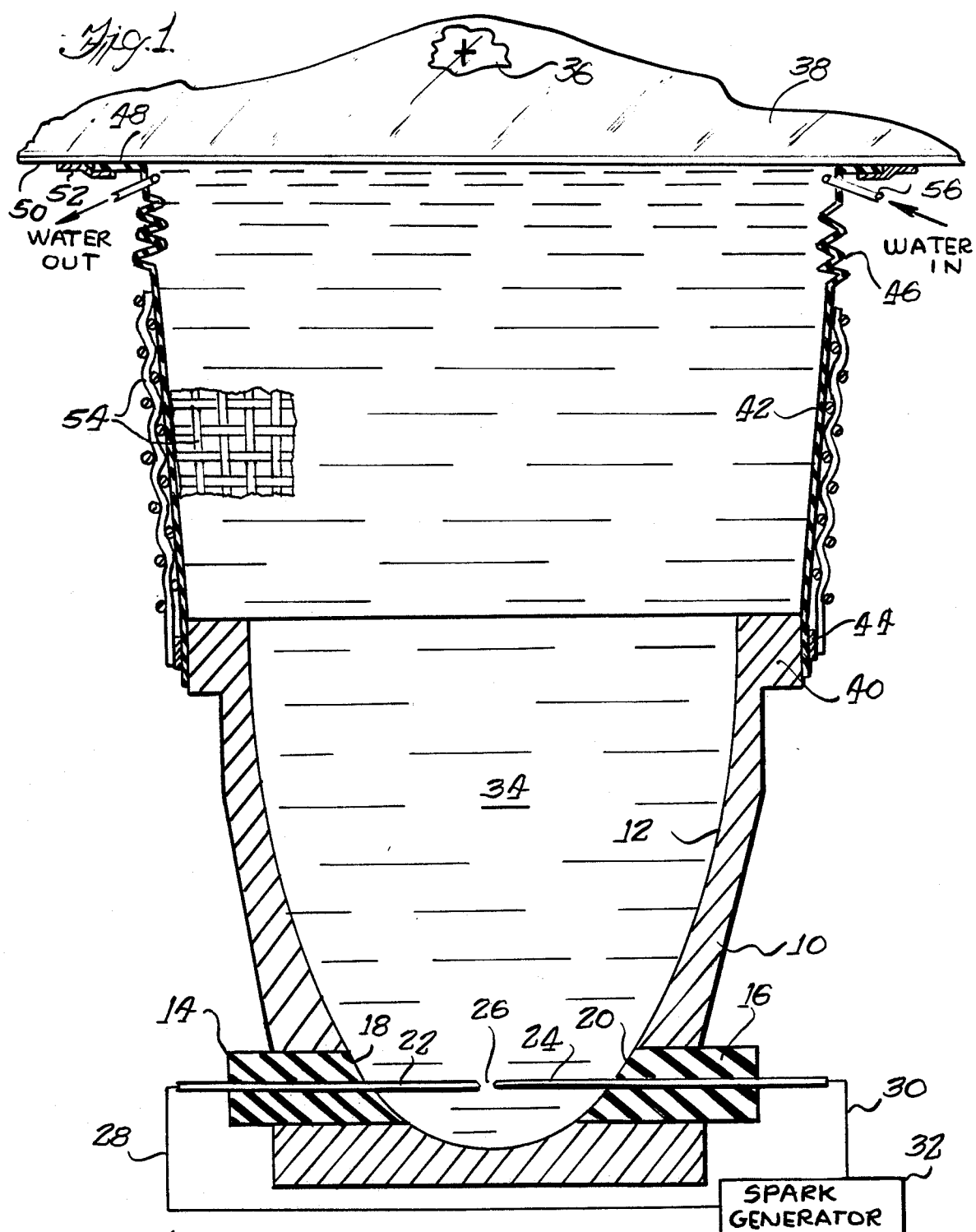

United States Patent [19]

Nowacki et al.

[11] Patent Number: 4,798,196
[45] Date of Patent: Jan. 17, 1989

[54] SHROUD FOR COUPLING KIDNEY STONE DISINTEGRATOR TO HUMAN BODY

[75] Inventors: Christopher Nowacki, Arlington Heights; Alfred G. Brisson, Kildeer, both of Ill.

[73] Assignee: Trutek Research, Inc., Lake Zurich, Ill.

[21] Appl. No.: 942,394

[22] Filed: Dec. 16, 1986

[51] Int. Cl.$^4$ ............................................. A61B 17/22
[52] U.S. Cl. ................................. 128/24 A; 128/328
[58] Field of Search .............................. 128/328, 24 A

[56] References Cited

U.S. PATENT DOCUMENTS 4,622,969 11/1986 Forssmann et al. ................. 128/328
4,662,375 5/1987 Hepp et al. .......................... 128/328

FOREIGN PATENT DOCUMENTS 3220751 12/1983 Fed. Rep. of Germany ...... 128/328
3444421 6/1986 Fed. Rep. of Germany ...... 128/328
2140693 12/1984 United Kingdom ................ 128/328

Primary Examiner—Ruth S. Smith
Attorney, Agent, or Firm—Robert M. Wolters

[57] ABSTRACT

An extracorporeal kidney stone disintegrator comprises an upwardly open ellipsoidal reflector having an open upper end. A spark gap is provided in said reflector at the first focus point thereof. A flexible waterproof shroud is fixed to the open end of the reflector and secured to the skin of a human body containing a concretion such as a kidney stone to be disintegrated. A body of water fills said reflector and said shroud and is in direct contact with the skin of said human body, the reflector being positioned relative to said body so that the concretion is at the second focus point of the reflector. Generation of a sprak across the spark gap causes generation of a shock wave focused on the concretion and coupled to the concretion by the body of water and by the tissues of the human body.

2 Claims, 1 Drawing Sheet

SHROUD FOR COUPLING KIDNEY STONE DISINTEGRATOR TO HUMAN BODY

BACKGROUND OF THE INVENTION

Kidney stones, and also naturally-occurring stones in the bladder and the ureter can be exquisitely painful, and often require surgical relief. Excision or destruction of stones in the bladder and sometimes in the ureter can be relatively easily accomplished, but removal of stones from the kidney is a major procedure.

Removal of stones from the kidney is a very serious and traumatic surgical procedure A large incision is made in the body. The kidney is essentially removed from the body and cut open. The stone or stones are then removed, whereupon the kidney is sutured and returned to the body, with the body then being sutured. Various efforts have been made to destroy or disintegrate kidney stones so that they can be excreted with the urine.

Chemotherapy is available as a non-invasive therapy for uric acid stones. In this therapy, the urine is alkalyzed, and the stone is dissolved over a substantial period of time. This requires detection of the stone before an acute phase is reached.

The next step was the use of ultrasound or an electrohydraulic shock wave produced by discharging a capacitor across a spark gap under water or other suitable liquid. Early efforts required invasion of the body, either through the urethra or through a surgical incision.

Subsequently, efforts have been made for the extracorporeal destruction of kidney stones through the use of a focused shock wave. In U.S. Pat. No. 3,942,531, for example, a reflector is used which is a portion of an ellipsoid. The spark gap is located at the first focus point of the ellipsoid, and the ellipsoid is positioned relative to the body so that the kidney stone or other calculus or concretion is at the second focus point of the ellipsoid. The reflector is filled with water. Discharge of a spark across the gap causes rapid vaporization of a portion of the water, and resultant generation of a shock wave which is focused by the reflector on the kidney stone. The shock wave travels through the water in the ellipsoidal reflector, and through the human tissues to the kidney stone. A repetition of the spark gap shock wave generation over a period of perhaps an hour, is necessary to destroy a kidney stone.

Problems exist in coupling the water in the ellipsoidal reflector to the human body for the most efficient transfer of energy into the human body and to the kidney stones. Previous efforts have utilized structures including a diaphragm over the otherwise open end of the ellipsoidal reflector

OBJECTS AND SUMMARY OF THE PRESENT INVENTION

It is an object of the present invention to provide structure for coupling an extracorporeal kidney stone disintegrator to the human body by highly efficient means insuring a maximum transfer of energy to the body.

More particularly, it is an object to provide such a kidney stone disintegrator in which an ellipsoidal reflector filled with water is coupled to the human body by means of a flexible shroud also filled with water, wherein the water directly contacts the skin of the human body.

In accordance with the present invention, an upwardly opening ellipsoidal reflector is filled with water and is provided with a spark gap for the generation of an electrohydraulic shock wave upon discharge of a capacitor across the spark gap. The open upper end of the ellipsoidal reflector is connected by a flexible shroud such as of elastomeric or plastic resin construction directly to the skin of the human body. The shroud is flexible so that the relative positions of the reflector and of the body can be adjusted to place the kidney stone at the second focus point of the ellipsoidal reflector, the spark gap being at the first focus point. The shroud is provided with a flange which may be secured to the skin of the body by means such as waterproof adhesive tape.

THE DRAWINGS

Figure 2:
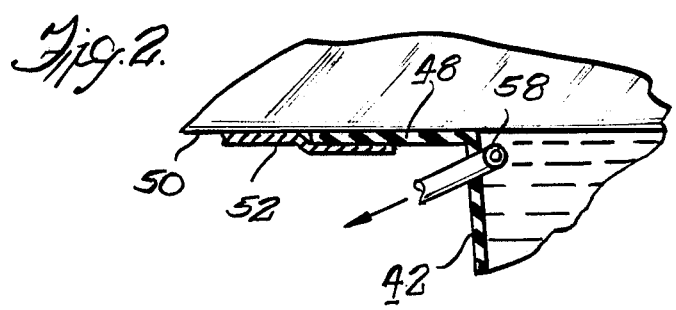

The invention will best be understood with reference to the following specification when taken in connection with the accompanying drawings wherein FIG. 1 is a longitudinal sectional view through an electrohydraulic shock wave generator, including an ellipsoidal reflector, and further including a shroud coupling the generator to the human body; and FIG. 2 is an enlarged fragmentary view of a portion of FIG. 1.

DETAILED DISCLOSURE OF THE ILLUSTRATED EMBODIMENT

Directing attention first to FIG. 1, there will be seen a metal base or block 10 having a hollow interior in the form of a truncated ellipsoidal reflector 12. Suitable means (not shown) is provided for filling the reflector with water, and for draining the reflector. Insulating members 14 and 16 are inserted into the reflector, and the inner ends thereof comprise continuations of the surface of the reflector as at 18 and 20, respectively. The insulating members 14 and 16 respectively carry conductive metal rods 22 and 24 aligned with but spaced apart at their inner ends to form a spark gap 26. The outer end of the rods extend exteriorally of the insulating members 14 and 16 and are respectively connected by wires 28 and 30 to a spark generator 32. The spark generator, as is known in the art, comprises a capacitor, means for charging the capacitor to a high voltage, and means for discharging the capacitor through the wires 28 and 30, and the conductive rods 22 and 24 to generate a spark across the spark gap 26. A spark jumping across the spark gap generates a shock wave in water 34 in the reflector, which shock wave is reflected by the ellipsoidal reflector 12 to concentrate the shock wave at the second focus point of the reflector, the latter being positioned carefully on a kidney stone or other concretion 36 in a human body 38.

The upper end of the body 10 is open, and is provided with a rim 40 to which a generally cylindrical elastomeric shroud 42 is secured by means such as a clamping band 44. Preferably the shroud tapers outwardly somewhat from bottom to top, and is provided in the upper wall portion thereof with an accordian pleated section 46 for flexibility and compressibility. The shroud is provided at its upper end with an outwardly directed, substantially right-angle flange 48 which presses against the skin 50 of the human body, and which is secured to the skin by means such as a waterproof adhesive tape 52. As will be apparent in FIG. 1 and particularly in FIG. 2 the adhesive tape is wide enough so that substantially one half of it is adhered to the outer surface of the flange 48, while the balance thereof is adhered to the skin 50. The water 34 in the reflector 12 extends on up into the shroud 42 and into engagement with the skin 50. Although the vertical dimensions are somewhat exaggerated in FIG. 1, there will be a substantial weight of water, and optionally a semi-rigid lattice 54 of wire, or preferably plastic, surrounds the shroud 42 from the band 44 up to a position adjacent the lower portion of the accordian pleats 46 to provide additional support.

Alternatively, the lower portion of the shroud can be made rather thick for remaining upright without external support. Similarly, the upper portion can be made thin for flexibility as an alternative to the accordion pleats.

A tubular inlet 56 for directing fresh water into the shroud and adjacent the sin is provided on one side of the shroud, and may be formed integrally therewith. Substantially diametrically opposite thereto is an exit fitting 58 for removal of water. A certain amount of gas is released from the water upon repetitive sparking across the gap 26. The gas inherently rises to the top of the water, and tends to collect on the skin 50, where it would inhibit the transfer of energy. The water inlet 56 is aimed slightly upwardly so as to cause a fresh flow of water across the skin, whereby the water flow in through the inlet at 56 and out through the outlet 58 carries out gas bubbles formed by the spark.

The shroud may be elastomeric in nature, or it may be of plastic resin material. Means other than adhesive tape may be used to secure the shroud to the skin of the human body, such as an adhesive applied directly to the upper surface of the flange 42. A Further alternative is to maintain the water 34 in the shroud at somewhat less than atmospheric pressure at the top of the shroud, whereby pressure differential will hold the shroud against the body. The elastomeric or plastic resin nature of the shroud provides inherent flexibility which allows the reflector 12 and body 10 to be moved relative to the human body 38 to position the second focus point of the ellipsoidal reflector precisely on the kidney stone 36. Such movement may be up and down, from side to side, or tilting. An important factor is that the water is in direct contact with the human skin. Since the human body is on the order of 80-85% water, coupling through the water in the reflector and in the shroud directly to the skin of the human body provides a highly efficient transfer of energy from within the relfector and shroud into the body and to the kidney stone 36.

The term "kidney stone" as used herein is to be understood broadly as any concretion within the urinary system, whether in a kidney, the ureter, the bladder or the urethra.

The specific example of the invention as herein shown and described is for purposes of illustration only. Various changes in structure will no doubt occur to those skilled in the art, and will be understood as forming a part of the present invention insofar as they fall within the spirit and scope of the appended claims The invention is claimed as follows:

1. An extracorporeal kidney stone disintegrator comprising an upwardly opening ellipsoidal reflector having a first focus point therein and a second focus point disposed above the reflector, said reflector having an open upper end, means providing a spark gap in said reflector at the first focus point thereof, a flexible waterproof shroud fixed to said open upper end of said reflector having an outwardly extending integral peripheral flange at an upper end of said shroud, means securing and sealing said flange directly to the skin of a human body containing a concretion such as a kidney stone to be disintegrated, and a body of water filling said reflector and said shroud and in direct contact with the skin of said human body, said reflector being positioned relative to said body so that the concretion is at the second focus point of the reflector, generation of a spark across said spark gap causing generation of a shock wave focussed on said concretion and coupled to said concretion by said body of water and by the tissues of said human body, and an external support surrounding and embracing said shroud.

2. A kidney stone disintegrator as set forth in claim 1 wherein said support comprises a lattice.

* * * * *